(12) United States Patent
Gonda et al.

(10) Patent No.: US 7,214,635 B2
(45) Date of Patent: May 8, 2007

(54) CAO-MGO-SIO$_2$-BASED BIOACTIVE GLASS AND SINTERED CALCIUM PHOSPHATE GLASS USING SAME (75) Inventors: Yukiko Gonda, Tokyo (JP); Tetsuro Ogawa, Tokyo (JP); Tadashi Kokubo, 50, Umegaoka 2-chome, Nagaokakyo-shi, Kyoto (JP)

(73) Assignees: PENTAX Corporation, Tokyo (JP); Tadashi Kokubo, Kyoto (JP)

( * ) Notice: Subject to any disclaimer, the term of this patent is extended or adjusted under 35 U.S.C. 154(b) by 0 days.

(21) Appl. No.: 10/962,557

(22) Filed: Oct. 13, 2004

(65) Prior Publication Data
US 2005/0079226 A1 Apr. 14, 2005

(30) Foreign Application Priority Data
Oct. 14, 2003 (JP) ............................. 2003-354023

(51) Int. Cl.
C04B 35/447 (2006.01)
C03C 3/078 (2006.01)

(52) U.S. Cl. .................. 501/1; 501/5; 501/57; 501/65; 501/72; 424/602

(58) Field of Classification Search .................. 501/1, 501/57, 72, 65, 5; 424/682, 724, 602
See application file for complete search history.

(56) References Cited

U.S. PATENT DOCUMENTS

| | | | |
|---|---|---|---|
| 3,981,736 A | 9/1976 | Broemer et al. | |
| 4,135,935 A | 1/1979 | Pfeil et al. | |
| 4,329,113 A | 5/1982 | Ayache et al. | |
| 4,437,192 A | 3/1984 | Fujiu et al. | |
| 4,443,550 A | 4/1984 | Kume et al. | |
| 4,497,629 A | 2/1985 | Ogino et al. | |
| 4,652,534 A | 3/1987 | Kasuga | |
| 4,708,652 A | 11/1987 | Fujiu et al. | |
| 4,731,394 A | 3/1988 | Vogel et al. | |
| 4,783,429 A * | 11/1988 | Shibuya et al. | 501/5 |
| 4,783,550 A | 11/1988 | DiCosimo et al. | |
| 4,871,384 A | 10/1989 | Kasuga | |
| 4,960,773 A * | 10/1990 | Korbonits et al. | 514/234.2 |
| 5,120,340 A | 6/1992 | Ducheyne et al. | |
| 5,125,971 A | 6/1992 | Nonami et al. | |
| 5,232,878 A * | 8/1993 | Kasuga et al. | 501/10 |

(Continued)

FOREIGN PATENT DOCUMENTS

DE 0247574 7/1987

(Continued)

OTHER PUBLICATIONS

English language Abstract of WO 03/01849.

(Continued)

Primary Examiner—Karl Group
(74) Attorney, Agent, or Firm—Greenblum & Bernstein, P.L.C.

(57) ABSTRACT

A bioactive glass having a composition substantially comprising 20 to 40 mol % of CaO, 40 to 60 mol % of SiO$_2$, and 10 to 20 mol % of MgO is high in bioactivity and mechanical strength, and a sintered calcium phosphate glass using the bioactive glass as a sintering aid is excellent in biocompatibility and mechanical strength.

8 Claims, 3 Drawing Sheets

U.S. PATENT DOCUMENTS

| | | | |
|---|---|---|---|
| 5,336,642 A * | 8/1994 | Wolcott | 501/3 |
| 5,344,456 A * | 9/1994 | Nonami et al. | 623/23.72 |
| 5,356,436 A | 10/1994 | Nonami et al. | |
| 5,634,956 A | 6/1997 | Suh et al. | |
| 5,658,332 A | 8/1997 | Ducheyne et al. | |
| 5,948,129 A | 9/1999 | Nonami et al. | |
| 5,981,412 A | 11/1999 | Hench et al. | |
| 6,130,178 A | 10/2000 | Andrus et al. | |
| 6,228,386 B1 | 5/2001 | Yang | |
| 6,306,785 B1 * | 10/2001 | Nonami et al. | 501/64 |
| 6,482,427 B2 | 11/2002 | Yang | |
| 6,875,715 B2 * | 4/2005 | Nishikawa et al. | 501/72 |
| 2004/0235637 A1 | 11/2004 | Berger et al. | |
| 2005/0009682 A1 | 1/2005 | Zimmer et al. | |

FOREIGN PATENT DOCUMENTS

| | | | |
|---|---|---|---|
| EP | 0577342 | | 1/1994 |
| EP | 1434742 | | 4/2003 |
| GB | 1441082 | | 6/1976 |
| GB | 2080281 | | 2/1982 |
| JP | 60-161368 | | 8/1985 |
| JP | 60-239341 | | 11/1985 |
| JP | 61-197463 | | 9/1986 |
| JP | 61-205637 | | 9/1986 |
| JP | 61205637 | * | 9/1986 |
| JP | 61-205637 | * | 11/1986 |
| JP | 62-052163 | | 3/1987 |
| JP | 63-242944 | | 10/1988 |
| JP | 3-37171 | | 2/1991 |
| JP | 3-090152 | | 4/1991 |
| JP | 4-036107 | | 2/1992 |
| JP | 4-036107 | * | 6/1992 |
| JP | 5-105463 | | 4/1993 |
| JP | 06-030984 | | 2/1994 |
| JP | 6-22574 | | 3/1994 |
| JP | 7-232930 | | 9/1995 |
| JP | 10-067627 | | 3/1998 |
| JP | 2898331 | | 3/1999 |
| JP | 2934090 | | 5/1999 |
| JP | 2000-072572 | | 3/2000 |
| JP | 2002-072572 | | 3/2000 |
| JP | 2001-130927 | | 5/2001 |
| JP | 3308355 | | 5/2002 |
| JP | 2002-206319 | | 7/2002 |
| WO | 94/04657 | | 3/1994 |
| WO | 03/018496 | | 3/2003 |
| WO | 03/031356 | | 4/2003 |
| WO | 03/062163 | | 7/2003 |

OTHER PUBLICATIONS

English language Abstract of WO 03/062163.
English Language Abstract of JP 2000-072572, published Mar. 7, 2000.
English Language Abstract of JP 63-242944, published Oct. 7, 1988.
English Language Abstract of JP 10-067627, published Mar. 10, 1998.
English Language Abstract of JP 06-030984, published Feb. 8, 1994.
English Language Abstract of JP 2001-130927, published May 15, 2001.
English Language Abstract of JP 61-197463, published Sep. 1, 1986.
English Language Abstract of DD 0247574, published Jul. 15, 1987.
I.B. Leonor et al., "Novel Starch Thermoplastic/Bioglass Composites: Mechanical Properties, Degradation Behavior and *In-Vitro* Bioactivity", Journal of Materials Science: Materials in Medicine, vol. 13, pp. 939-945 (2002).
A.J. Salinas et al., "In Vitro Bioactivity of Glass and Glass-Ceramics of the $3CaO \cdot P_2O_5\text{-}CaO \cdot SiO_2\text{-}CaO\text{-}MgO \cdot 2SiO_2$ System", Biomaterials, vol. 21, pp. 251-257 (2000).
J.D. Santos et al., "Liquid Phase Sintering of Hydoxyapatite by Phosphate and Silicate Glass Additions: Structure and Properties of the Composites", Journal of Materials Science: Materials in Medicine, vol. 6, pp. 348-352 (1995).
J.D. Santos et al., "Reinforcement of Hydroxyapatite by Adding $P_2O_5$-CaO Glasses with $NA_2O$, $K_2O$ and MgO", Journal of Materials Science: Materials in Medicine, vol. 7, pp. 187-189 (1996).
English language Abstract of JP 2001-130927.
English language Abstract of JP 5-105463.

* cited by examiner

CAO-MGO-SIO$_2$-BASED BIOACTIVE GLASS AND SINTERED CALCIUM PHOSPHATE GLASS USING SAME

FIELD OF THE INVENTION

The present invention relates to a CaO—MgO—SiO$_2$-based bioactive glass usable in bone-restoring materials such as artificial joints, artificial dental roots and artificial bones, and a sintered calcium phosphate glass using the bioactive glass.

BACKGROUND OF THE INVENTION

When an artificial material is implanted in a damaged bone of a living body, the material is generally surrounded by membranes of collagen fibers and thus isolated from neighboring bones. There have been known some artificial materials, which are not isolated by such fibrous membranes and connect to bones in a living body strongly and naturally. Examples of such artificial materials include Na$_2$O—CaO—SiO$_2$—P$_2$O$_5$-based bioglasses, sintered hydroxyapatites (Ca$_{10}$(PO$_4$)$_6$(OH)$_2$), and crystallized glasses A-W containing apatite microcrystals and β-wollastonite microcrystals (CaO, SiO$_2$). These materials are referred to as bioactive ceramics, and some of them have been put into practical use as important bone-restoring materials.

Among the bioactive ceramics, sintered hydroxyapatites are well known for high biocompatibility and have been most widely used in clinical applications as bone supplements, replacement bone, artificial vertebrae, artificial joints, bioactive coating materials of artificial dental roots, etc. Also methods of producing the sintered hydroxyapatites have been widely studied. With demand for more biocompatible artificial bones increasing in recent years, however, it is desired to develop a bone-restoring apatite material containing a magnesium ion or a carbonate ion like a bone in a living body.

The carbonated apatites are so lower in decomposition temperature than the hydroxyapatites that they are sintered at relatively low temperatures to provide carbonated apatite ceramics. JP 2000-72572 A discloses a molded implant produced by plastically working a sintered apatite body, and a method for producing the molded implant, which comprises the steps of sintering an apatite at 900° C. or lower, charging the sintered apatite into a predetermined mold, and plastically working the sintered apatite at 300 to 780° C. Because the sintering temperature is low in this method, a carbonated or fluorinated apatite with a low decomposition temperature can be used to produce the implant having high biocompatibility. Further, JP 3308355 B discloses a method for producing a sintered carbonated apatite, which comprises sintering at 600 to 850° C. However, these implants mainly comprise the apatites without other crystal phases, thereby having low mechanical strength.

Effective methods for producing dense sintered bodies at low temperatures include liquid phase sintering methods using glasses as sintering aids. By using the liquid phase sintering methods, sintered apatites with improved mechanical strength can be produced such that a bioactive glass is softened around main crystals of an apatite such as a carbonated apatite in a bone-restoring ceramic material and generates crystals between the main crystals. Conventionally, non-bioactive glasses are used as the sintering aids of the sintered hydroxyapatite body. However, because the non-bioactive glasses have high glass transition temperatures and/or crystallization temperatures, they cannot generate preferable crystals by sintering at temperatures lower than the decomposition temperatures of the carbonated apatites. JP 2934090 B discloses a biocompatible implant having a bending strength of 40 MPa or more, which is produced by adding a calcium phosphate-based glass frit to a hydroxyapatite and by burning the resultant mixture. However, the biocompatible implant has a high porosity of 5 to 55%, and this method cannot produce a dense biocompatible implant. Proposed in Japanese Patent Application No. 2002-206319 corresponding to U.S. Ser. No. 10/618,687 are a bioactive glass low in glass transition temperature and/or crystallization temperature, and a sintered calcium phosphate body using the bioactive glass, which has high biocompatibility, large mechanical strength, and excellent sinterability. However, the bioactive glass cannot be sufficiently softened at the decomposition temperature of the carbonated apatite or lower, and thus sintered carbonated apatite bodies using the bioactive glass are not sufficient in mechanical strength.

OBJECT OF THE INVENTION

Accordingly, an object of the present invention is to provide a bioactive glass having a low glass transition temperature and/or a low crystallization temperature, and a crystallized glass-composite, sintered calcium phosphate body using the bioactive glass, which is high in biocompatibility and mechanical strength, and can be produced at low temperatures.

SUMMARY OF THE INVENTION

As a result of intense research in view of the above object, the inventors have found that a bioactive glass having a composition substantially comprising 20 to 40 mol % of CaO, 40 to 60 mol % of SiO$_2$, and 10 to 20 mol % of MgO has a low glass transition temperature and/or a low crystallization temperature, and that a sintered calcium phosphate glass with high biocompatibility and large mechanical strength can be produced at a low temperature by using the bioactive glass as a sintering aid. The present invention has been accomplished by the findings.

Thus, the bioactive glass of the present invention has a composition substantially comprising 20 to 40 mol % of CaO, 40 to 60 mol % of SiO$_2$, and 10 to 20 mol % of MgO.

The bioactive glass substantially comprising CaO, SiO$_2$, and MgO has high bioactivity and large mechanical strength. It is preferred that the bioactive glass of the present invention further comprises at least one of CaF$_2$, Na$_2$O, and B$_2$O$_3$. The bioactive glass containing these components has a low glass transition temperature, and a large difference ΔT between the glass transition temperature and its crystallization initiation temperature. The glass transition temperature is preferably 650 to 750° C. The difference ΔT between the glass transition temperature and the crystallization initiation temperature is preferably 70 to 250° C. The bioactive glass having the low glass transition temperature can be used as a sintering aid even for sintering carbonated apatites, etc. with low decomposition temperatures. When the difference ΔT is sufficiently large, a dense sintered body can be produced without precise sintering temperature control. It is preferred that the bioactive glass is crystallized to generate a β-wollastonite crystal and a diopside crystal in view of increasing the mechanical strength. To generate the β-wollastonite crystal and the diopside crystal easily, the bioactive glass preferably has a P$_2$O$_5$ content of 5 mol % or less.

A sintered calcium phosphate glass of the present invention comprises the above bioactive glass as a sintering aid.

The sintered calcium phosphate glass of the present invention preferably comprises at least one calcium phosphate component selected form the group consisting of hydroxyapatites, carbonated apatites and tricalcium phosphates. In the sintered calcium phosphate glass, the bioactive glass used as the sintering aid preferably generates a β-wollastonite crystal and a diopside crystal.

The bioactive glass of the present invention has a composition substantially comprising 20 to 40 mol % of CaO, 40 to 60 mol % of $SiO_2$, and 10 to 20 mol % of MgO, thereby showing high bioactivity and large mechanical strength. The bioactive glass can generate a β-wollastonite crystal and a diopside crystal to further increase the mechanical strength. Thus, by using the bioactive glass as a sintering aid for calcium phosphate, the sintered calcium phosphate glass excellent in biocompatibility and mechanical strength can be produced at a low temperature.

BRIEF DESCRIPTION OF THE DRAWINGS

FIGS. 2(a) to 2(d) are schematic, cross-sectional views showing the changes of particle boundaries in the process of sintering a green body composed of hydroxyapatite particles and CaO—$SiO_2$-based glass particles, wherein

DETAILED DESCRIPTION OF THE PREFERRED EMBODIMENTS

[1] Bioactive Glass

The bioactive glass of the present invention has a composition comprising 20 to 40 mol % of CaO, 40 to 60 mol % of $SiO_2$, and 10 to 20 mol % of MgO, and preferably has a composition comprising 30 to 40 mol % of CaO, 40 to 50 mol % of $SiO_2$, and 10 to 20 mol % of MgO. What is meant by "the bioactive glass has a composition comprising 20 to 40 mol % of CaO, 40 to 60 mol % of $SiO_2$, and 10 to 20 mol % of MgO" is that the bioactive glass contains CaO, $SiO_2$ and MgO in the above-described percentages as main components, and may contain other components unless they have adverse effects on the present invention. The total content of CaO, $SiO_2$ and MgO is preferably 90 mol % or more, more preferably 95 mol % or more. The bioactive glass with such a composition has bioactivity preferable for use as a bioactive material, and has mechanical strength and sinterability preferable for use as a sintering aid in a sintered calcium phosphate glass.

When the bioactive glass comprising CaO and MgO is implanted in a damaged region of a bone, a calcium ion and a magnesium ion are eluted from the bioactive glass to show an improved bioactivity. The bioactive glass, which has lost part of the calcium ions and the magnesium ions by elution, forms SiOH groups on its surface. The SiOH groups forms the basis of nucleation of calcium phosphate crystals, whereby the bioactive glass can strongly connect to cortical bones.

The bioactive glass of the present invention contains CaO, $SiO_2$ and MgO as main components. Thus, the composition of the bioactive glass is similar to that of a lowest-melting-point β-wollastonite-diopside mixture, whereby the bioactive glass easily generates a β-wollastonite crystal and a diopside crystal at a crystallization temperature. The bioactive glass preferably generates the β-wollastonite crystal and the diopside crystal at the crystallization temperature, because the crystals have needle-like structures and further increase the mechanical strength of the sintered calcium phosphate glass as compared with other crystals. In the case of adding a large amount of $P_2O_5$ to improve biocompatibility like conventional methods, the β-wollastonite crystal and the diopside crystal are often not fully formed at the crystallization temperature.

The bioactive glass of the present invention has improved biocompatibility due to the increased CaO and MgO content, requiring no $P_2O_5$ as a main component. In addition, $P_2O_5$ often elevates the glass transition temperature and/or the crystallization temperature of the bioactive glass. Accordingly, it is preferred that the bioactive glass does not contain a large amount of $P_2O_5$. By not adding a large amount of $P_2O_5$ and by adding minor components such as $CaF_2$ (described later) to the bioactive glass, the glass transition temperature and/or the crystallization temperature of the bioactive glass can be lowered and the β-wollastonite crystal and the diopside crystal can be easily generated. The $P_2O_5$ content of the bioactive glass is preferably 5 mol % or less.

In the case of using the bioactive glass as the sintering aid for calcium phosphate, a crystal of tricalcium phosphate may be generated at the crystallization temperature of the bioactive glass. Tricalcium phosphate is similar to hydroxyapatites in physical properties, solubility and biocompatibility. Further, the crystal of tricalcium phosphate can improve the biocompatibility of the sintered calcium phosphate glass.

The sinterability is improved in a case where the sintering aid of the bioactive glass has (1) a low glass transition temperature Tg, (2) a crystallization initiation temperature $Tc_0$ remarkably lower than the decomposition temperature of calcium phosphate, and (3) a large difference ΔT between the glass transition temperature Tg and the crystallization initiation temperature $Tc_0$. In the present invention, the term "crystallization initiation temperature" means a temperature at which the bioactive glass begins to generate a crystal such as the β-wollastonite crystal and the diopside crystal. Specifically, the crystallization initiation temperature is defined as a temperature of intersection of a base line and a tangential line at an inflection point of an exothermic peak in a differential thermal analysis curve. The term "crystallization temperature" means a temperature at which the crystal is generated, with a definition as a temperature of an exothermic peak in a differential thermal analysis curve.

To evaluate the effects of $Na_2O$, etc. in a composition comprising CaO, $SiO_2$ and MgO on the glass transition temperature, etc., a bioactive glass composed of 34.1 mol % of CaO, 50 mol % of $SiO_2$, and 15.9 mol % of MgO was experimented below.

Figure 1:
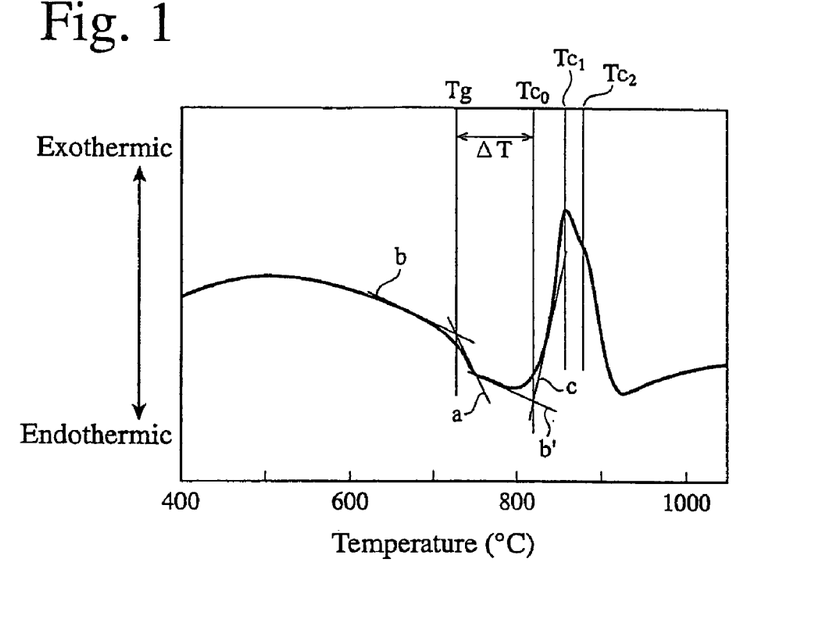
FIG. 1 is a graph showing the result of differential thermal analysis of a CaO—MgO—$SiO_2$-based glass.

FIG. 1 is a graph showing the exothermic and endothermic changes with temperatures from 100° C. to 1,100° C. in the differential thermal analysis of the bioactive glass composed of 34.1 mol % of CaO, 50 mol % of $SiO_2$, and 15.9 mol % of MgO. The bioactive glass generates heat in a temperature range where the curve rises, and absorbs heat in a temperature range where the curve declines. In the differential thermal analysis (DTA) curve, an intersection of a base line b and a tangential line a at the inflection point in a transition region is defined as the glass transition temperature Tg. A temperature of an exothermic peak is the crystallization temperature Tc. When the curve has a plurality of exothermic peaks, temperatures corresponding to the peaks are the crystallization temperatures $Tc_1$, $Tc_2$, . . . . Further, the crystallization initiation temperature $Tc_0$ is obtained from the intersection of a tangential line c at the inflection point in the declining of the exothermic peak and a base line b' in a transition region of the DTA curve. ΔT represents the difference between the glass transition temperature Tg and the crystallization initiation temperature $Tc_0$. The bioactive glass shows a softening behavior in a temperature region between the glass transition temperature Tg and the crystallization initiation temperature $Tc_0$.

The bioactive glass with a low glass transition temperature Tg can be used as a sintering aid for the carbonated apatite, etc. having a low decomposition temperature. To easily carry out the sintering at a temperature lower than the decomposition temperature of calcium phosphate and higher than the crystallization initiation temperature $Tc_0$, the crystallization initiation temperature $Tc_0$ is preferably lower than the decomposition temperature with a difference of 400° C. or more. The glass transition temperature Tg is preferably 750° C. or lower, more preferably 650 to 750° C., further preferably 650 to 725° C. The lower limit of the glass transition temperature Tg is preferably about 200° C. from the viewpoint of the glass stability though not particularly restrictive. The bioactive glass of the present invention preferably has a large difference ΔT between the glass transition temperature Tg and the crystallization initiation temperature $Tc_0$. When the difference ΔT is large, a dense sintered body is easily obtained without needing precise control of the sintering temperature. The difference ΔT of the bioactive glass is preferably 70 to 250° C., more preferably 80 to 250° C., further preferably 100 to 250° C.

The addition of $CaF_2$ to the bioactive glass can lower its glass transition temperature Tg and increase the difference ΔT. With $CaF_2$ added, the glass transition temperature Tg and the crystallization initiation temperature $Tc_0$ are both lowered, and the reduction of the crystallization initiation temperature $Tc_0$ is smaller than that of the glass transition temperature Tg. Thus, the glass transition temperature Tg is lowered, and the difference ΔT is increased. The amount of $CaF_2$ added is preferably 5 mol % or less, more preferably 3 mol % or less. The lower limit of the amount of $CaF_2$ is preferably 0.1 mol %. When the amount of $CaF_2$ added is less than 0.1 mol %, no effects of adding $CaF_2$ are substantially obtained.

The glass transition temperature Tg of the bioactive glass may be lowered by adding $Na_2O$. However, an excess amount of $Na_2O$ often inhibits the formation of the β-wollastonite crystal and the diopside crystal. Thus, the amount of $Na_2O$ is preferably 5 mol % or less, more preferably 1 mol % or less. The lower limit of the amount of $Na_2O$ is preferably 0.1 mol %. When the amount of $Na_2O$ added is less than 0.1 mol %, no effects of adding $Na_2O$ are substantially obtained.

$B_2O_3$ may be added to the bioactive glass. The addition of a small amount of $B_2O_3$ can lower its glass transition temperature Tg and increase the difference ΔT like the addition of $CaF_2$. The amount of $B_2O_3$ added is preferably 5 mol % or less, more preferably 1 mol % or less. The lower limit of the amount of $B_2O_3$ is preferably 0.1 mol %. When the amount of $B_2O_3$ added is less than 0.1 mol %, no effects of adding $B_2O_3$ are substantially obtained.

At least one of $CaF_2$, $Na_2O$ and $B_2O_3$ is preferably added to the bioactive glass of the present invention. The bioactive glass with the preferred glass transition temperature Tg and the preferred difference ΔT can be obtained by adding an appropriate combination of $CaF_2$, $Na_2O$ and $B_2O_3$. The total amount of $CaF_2$, $Na_2O$ and $B_2O_3$ is preferably 0.1 to 5 mol %, more preferably 0.1 to 2 mol %.

An inorganic compound such as $K_2O$ may be added to the bioactive glass. It is preferable to use an inorganic compound that does not increase the glass transition temperature Tg and does not inhibit the formation of the β-wollastonite crystal and the diopside crystal.

There are no particular restrictions in methods for producing the bioactive glass of the present invention. The bioactive glass may be produced by methods described in JP 60-239341 A, etc. For example, a material powder mixture with a desired composition are put in a platinum crucible and heated at 1,200 to 1,600° C. for approximately 3 hours to obtain a molten glass. The molten glass is molded and annealed to produce the bioactive glass. Though not particularly restrictive, the shape of the bioactive glass may be in a shape of an ingot, a sphere, beads, particles, granules, etc. depending on the purposes. When the bioactive glass is used as a starting material for the sintered calcium phosphate glass of the present invention that will be described below, the diameter of the bioactive glass may be controlled by pulverization or classification.

[2] Sintered Calcium Phosphate Glass (1) Composition of Sintered Calcium Phosphate Glass The sintered calcium phosphate glass of the present invention comprises the sintering aid of the bioactive glass of the present invention in addition to calcium phosphate particles. The calcium phosphate particles are preferably particles of a hydroxyapatite, a carbonated apatite, tricalcium phosphate, or a mixture thereof. The carbonated apatite is particularly preferred because it can further increase the biocompatibility of the sintered calcium phosphate glass.

The average particle diameter of the calcium phosphate particles is preferably 1 to 100 μm, more preferably 10 to 20 μm. When the average particle diameter is less than 1 μm, the particles are likely to aggregate, making it difficult to classify the particles. When the average particle diameter is more than 100 μm, the mixture is not uniform and is poor in the sinterability. The calcium phosphate particles with a preferred average particle diameter may be prepared by a spray granulation method using calcium phosphate crystal grains, etc. The average grain size of the calcium phosphate crystal grains is preferably 1 μm or less, more preferably 10 to 500 nm.

The mass ratio of the bioactive glass to the calcium phosphate particles is preferably 0.1 to 10% by mass, more preferably 0.1 to 1% by mass. When the mass ratio of the bioactive glass is less than 0.1% by mass, the effect of accelerating the sintering is insufficient. When the mass ratio is more than 10% by mass, an unpreferable crystal phase is likely to be generated. The unpreferable crystal phases are those containing no needle crystals, those failing to improve the fracture toughness, those having no bioactivities, or those inhibiting the formation of the β-wollastonite crystal and the diopside crystal. The unpreferable crystal phase may be slightly generated unless it ruins the advantageous effects of the present invention. The bioactive glass may be in the form of pulverized glass particles. The average particle diameter of the glass particles is preferably 0.1 to 10 μm, more preferably 0.1 to 5 μm.

It is preferred that a needle β-wollastonite crystal and a needle diopside crystal are generated in the sintering aid of the bioactive glass at the crystallization temperature. These needle crystals can increase the fracture toughness of the sintered calcium phosphate glass. The percentage of the generated β-wollastonite and diopside crystals to the bioactive glass is preferably 10 to 100% by mass, more preferably 50 to 100% by mass. When the percentage is less than 10% by mass, the sintered calcium phosphate glass has an insufficient mechanical strength.

(2) Method for Producing Sintered Calcium Phosphate Glass

The sintered calcium phosphate glass of the present invention may be produced by a usual sintering method. The calcium phosphate particles and the bioactive glass particles may be wet-blended with zirconia balls and a solvent such as isopropyl alcohol and ethanol, and dried to obtain a mixture for sintering. The drying time is preferably 0.5 to 5 hours, more preferably 2 to 5 hours. The mixture is preferably put in a stainless steel die, etc. and press-molded and then cold-isostatic-pressed.

A green body thus obtained is sintered. The sintering temperature of the green body is preferably 700 to 1,300° C., more preferably 700 to 900° C. When the hydroxyapatite is heated, it is gradually deprived of hydroxyl groups at around 1,000° C. or higher, causing decomposition at around 1,300° C. or higher. Thus, in the case of using the hydroxyapatite as the calcium phosphate component, the sintering process is preferably carried out at a temperature lower than 1,000° C. When the carbonated apatite is heated, the carbonate moieties are eliminated at a temperature of around 900° C. or higher, which is lower than the elimination temperature of the hydroxyl groups of the hydroxyapatite. Thus, in the case of using the carbonated apatite as the calcium phosphate component, the sintering process is preferably carried out at a temperature lower than 900° C. The sintering time is preferably 0.5 to 10 hours, more preferably 2 to 5 hours.

Figure 2:
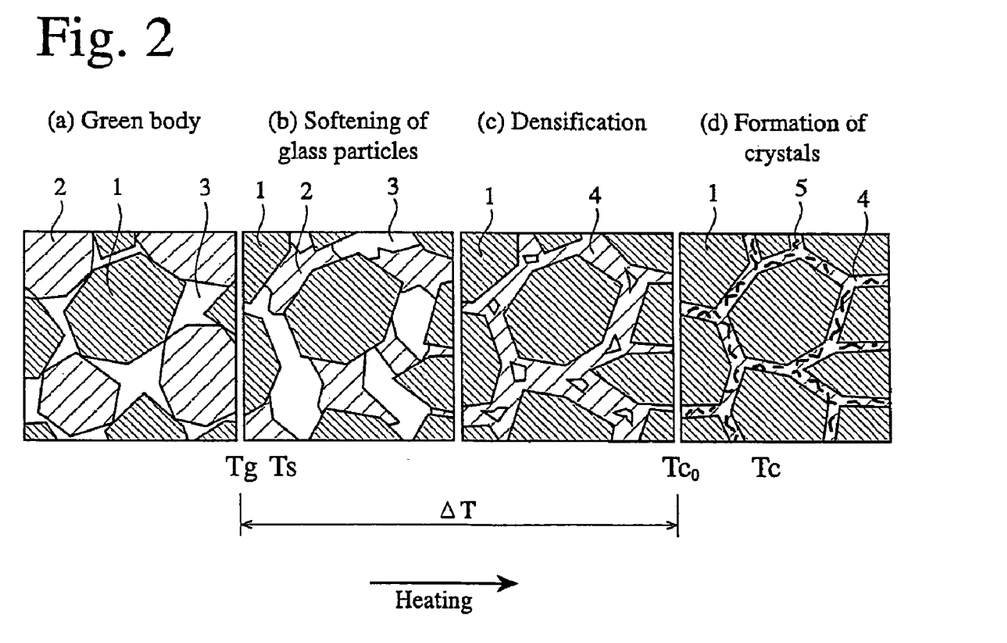
FIG. 2(a) shows the hydroxyapatite particles and the CaO—$SiO_2$-based glass particles at a temperature lower than the glass transition temperature.
FIG. 2(b) shows the particles at the glass softening temperature Ts.
FIG. 2(c) shows densification by sintering with the formation of a grain boundary phase (glassy phase)
FIG. 2(d) shows the formation of β-wollastonite crystals and diopside crystals after the temperature reaches a crystallization temperature.

As shown in FIG. 2(a), the calcium phosphate particles 1 and the glass particles 2 are uniformly distributed in the green body. When the green body is heated at the glass transition temperature $T_g$ or higher, the glass particles are softened at the glass softening temperature $T_s$ as shown in FIG. 2(b). When the green body is further heated, the softened glass particles penetrate into pores 3 between the calcium phosphate particles to cause densification, thereby forming grain boundary phases (glassy phases) 4 as shown in FIG. 2(c).

As shown in FIG. 2(d), when the sintering process proceeds and the green body is heated at a temperature higher than the crystallization initiation temperature $Tc_0$ at which at least part of the glass components are crystallized, crystals 5 are generated in the grain boundary phases at the crystallization temperature $T_c$ to form crystal phases. Because the sintering temperature is lower than the melting temperature and the decomposition temperature of the calcium phosphate throughout the sintering process, the calcium phosphate particles are not substantially decomposed or dissolved in the glass. Thus, the crystals of certain glass components such as the β-wollastonite and the diopside are generated between the calcium phosphate crystals, to provide the sintered, dense calcium phosphate glass. The heating rate is preferably constant, and is preferably 10° C./min or less, more preferably 5° C./min or less. The sintered calcium phosphate glass is preferably cooled in a furnace.

The present invention will be explained in more detail with reference to Examples below without intention of restricting the scope of the present invention.

EXAMPLE 1

34.1 mol % of $CaCO_3$ powder, 50.0 mol % of $SiO_2$ powder, and 15.9 mol % of MgO powder were mixed as shown in Table 1, and the resultant material powder mixture was melted at 1,560° C. for 1 hour or more to produce a bioactive glass ingot having a uniform composition.

EXAMPLES 2 TO 11

Each material powder mixture having a composition shown in Table 1 was melted at 1,400 to 1,560° C. for 1 hour or more to produce a bioactive glass ingot having a uniform composition.

TABLE 1

| | Composition (mol %) | | | | | | |
|---|---|---|---|---|---|---|---|
| No. | CaO | $SiO_2$ | MgO | $CaF_2$ | $P_2O_5$ | $Na_2O$ | $B_2O_3$ |
| Example 1 | 34.1 | 50.0 | 15.9 | — | — | — | — |
| Example 2 | 33.6 | 50.0 | 15.9 | 0.5 | — | — | — |
| Example 3 | 33.1 | 50.0 | 15.9 | 1.0 | — | — | — |
| Example 4 | 32.1 | 50.0 | 15.9 | 2.0 | — | — | — |
| Example 5 | 31.1 | 50.0 | 15.9 | 3.0 | — | — | — |
| Example 6 | 33.7 | 49.5 | 15.8 | — | — | 1.0 | — |
| Example 7 | 33.7 | 49.5 | 15.8 | — | — | — | 1.0 |
| Example 8 | 32.4 | 50.5 | 16.1 | — | 1.0 | — | — |
| Example 9 | 31.8 | 49.5 | 15.7 | 2.0 | 1.0 | — | — |
| Example 10 | 31.4 | 49.0 | 15.6 | 2.0 | — | 1.0 | 1.0 |
| Example 11 | 31.8 | 49.5 | 15.7 | 2.0 | — | 0.5 | 0.5 |

COMPARATIVE EXAMPLES 1 TO 5

Each material powder mixture having a composition shown in Table 2 was melted at 1,560° C. for 1 hour or more to produce a bioactive glass ingot having a uniform composition.

TABLE 2

| | Composition (mol %) | | | | | | |
|---|---|---|---|---|---|---|---|
| No. | CaO | $SiO_2$ | MgO | $CaF_2$ | $P_2O_5$ | $Na_2O$ | $B_2O_3$ |
| Comparative Example 1 | 49.5 | 49.5 | — | — | — | 1.0 | — |
| Comparative Example 2 | 47.5 | 47.5 | — | — | — | 5.0 | — |
| Comparative Example 3 | 49.5 | 50.0 | — | 0.5 | — | — | — |

TABLE 2-continued

| No. | Composition (mol %) | | | | | | |
|---|---|---|---|---|---|---|---|
| | CaO | $SiO_2$ | MgO | $CaF_2$ | $P_2O_5$ | $Na_2O$ | $B_2O_3$ |
| Comparative Example 4 | 49.0 | 49.5 | — | 0.5 | — | 1.0 | — |
| Comparative Example 5 | 49.5 | 49.0 | — | 0.5 | — | 1.0 | 1.0 |

Each bioactive glass of Examples 1 to 11 and Comparative Examples 1 to 5 was subjected to differential thermal analysis, to obtain the glass transition temperature Tg, the crystallization initiation temperature $Tc_0$, the crystallization temperatures Tc, and the difference $\Delta T$ between the glass transition temperature Tg and the crystallization initiation temperature $Tc_0$.

TABLE 3

| No. | Glass Transition Temperature Tg (° C.) | Crystallization Initiation Temperature $Tc_0$ (° C.) | Crystallization Temperature Tc (° C.)[1] | Difference $\Delta T$ between Tg and $Tc_0$ (° C.) |
|---|---|---|---|---|
| Example 1 | 749 | 829 | 855/885 | 80 |
| Example 2 | 737 | 838 | 869/891/1008 | 101 |
| Example 3 | 724 | 837 | 876/902 | 113 |
| Example 4 | 700 | 848 | 878/1004 | 148 |
| Example 5 | 693 | 845 | 867/1000 | 152 |
| Example 6 | 734 | 811 | 835/860/935 | 77 |
| Example 7 | 716 | 832 | 906/1009 | 116 |
| Example 8 | 749 | 827 | 867/909 | 78 |
| Example 9 | 705 | 908 | 926/(848/990) | 203 |
| Example 10 | 689 | 842 | 868/(809/888) | 153 |
| Example 11 | 696 | 868 | 885/(835/896) | 172 |
| Comparative Example 1 | 774.4 | 862.5 | 882.6 | 88.1 |
| Comparative Example 2 | 717.4 | 798.7 | 829.3 | 81.3 |
| Comparative Example 3 | 780.4 | 862.6 | 883.8 | 82.2 |
| Comparative Example 4 | 763.1 | 859.0 | 874.9 | 95.9 |
| Comparative Example 5 | 746.4 | 837.4 | 851.6/869.4 | 91.0 |

Note:
[1]Values in parentheses represent crystallization temperatures at small exothermic peaks.

Each bioactive glass of Examples 1 to 11 and Comparative Examples 1 to 5 was heated to the crystallization temperature, and the generated crystal phases were analyzed by X-ray structure analysis. The results are shown in Table 4.

TABLE 4

| No. | Crystal Phase Observed After Heating to Crystallization Temperature Tc |
|---|---|
| Example 1 | β-Wollastonite, Diopside |
| Example 2 | β-Wollastonite, Diopside |
| Example 3 | β-Wollastonite, Diopside |
| Example 4 | β-Wollastonite, Diopside |
| Example 5 | β-Wollastonite, Diopside |
| Example 6 | β-Wollastonite, Diopside |
| Example 7 | β-Wollastonite, Diopside |
| Example 8 | β-Wollastonite > Diopside |
| Example 9 | β-Wollastonite, Diopside |
| Example 10 | β-Wollastonite, Diopside |
| Example 11 | β-Wollastonite, Diopside |

TABLE 4-continued

| No. | Crystal Phase Observed After Heating to Crystallization Temperature Tc |
|---|---|
| Comparative Example 1 | β-Wollastonite »$Na_2CaSiO_4$ |
| Comparative Example 2 | β-Wollastonite »$Na_2CaSiO_4$, $Na_2Ca_2SiO_7$ |
| Comparative Example 3 | β-Wollastonite |
| Comparative Example 4 | β-Wollastonite »$Na_2CaSiO_4$ |
| Comparative Example 5 | β-Wollastonite, $Na_2CaSiO_4$ |

As shown in Table 4, the bioactive glasses of Examples 1 to 11 generated the β-wollastonite crystal and the diopside crystal.

EXAMPLE 12

The bioactive glass ingot of Example 4 was pulverized into particles having an average particle diameter of 1 to 2 µm. The bioactive glass particles were added in proportions of 1% and 5% by mass, respectively, to 100% by mass of agglomerated particles of hydroxyapatite nano-particles (available from Pentax Corporation, average diameter 15 µm). Each resultant mixture was wet-blended using isopropyl alcohol and zirconia balls, and dried to obtain powder for sintering. 0.2 g of each of the powders having different bioactive glass contents was placed in a stainless steel die, and uniaxially press-molded and cold-isostatic-pressed (CIP) to produce a disc-shaped green body having a diameter of 10 mm and a thickness of 2 mm. Each green body was sintered at 800° C. for 1 hour and at 900° C. for 4 hours, and cooled in a furnace to produce a sintered hydroxyapatite. The heating rate in the sintering was 5° C./min. Further, sintered hydroxyapatite bodies were produced in the same manner except for changing the sintering temperature to 1,000° C. or 1,100° C., respectively. The sintered hydroxyapatite bodies were subjected to X-ray analysis. The results of the X-ray analysis are shown in FIGS. 3 to 5.

COMPARATIVE EXAMPLE 6

Sintered hydroxyapatite bodies were produced in the same manner as in Example 12 except that only the agglomerated particles of hydroxyapatite nano-particles (available from Pentax Corporation, average diameter 15 µm) were sintered at 900° C., 1,000° C. or 1,100° C. for 4 hours. The sintered hydroxyapatite bodies were subjected to X-ray analysis. The results of the X-ray analysis are shown in FIGS. 3 to 5.

Figure 3:
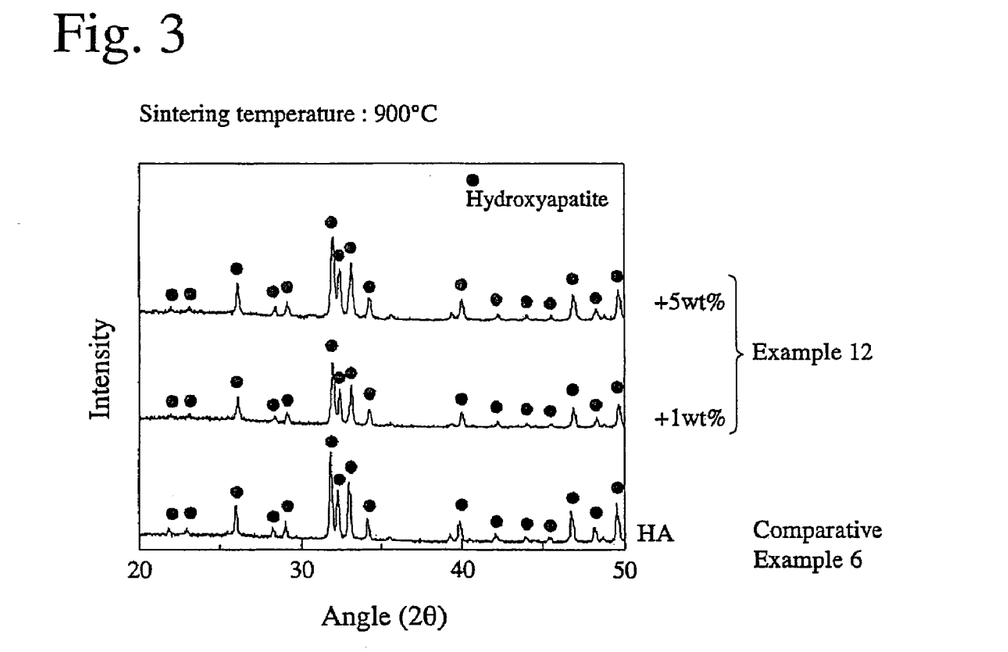
FIG. 3 is a graph showing the results of X-ray structure analysis of those sintered at 900° C., which are a sintered hydroxyapatite (HA), a sintered calcium phosphate glass containing 1% by mass of the bioactive glass of Example 4 (indicated by "+1 wt. %"), and a sintered calcium phosphate glass containing 5% by mass of the bioactive glass of Example 4 (indicated by "+5 wt. %")
Figure 4:
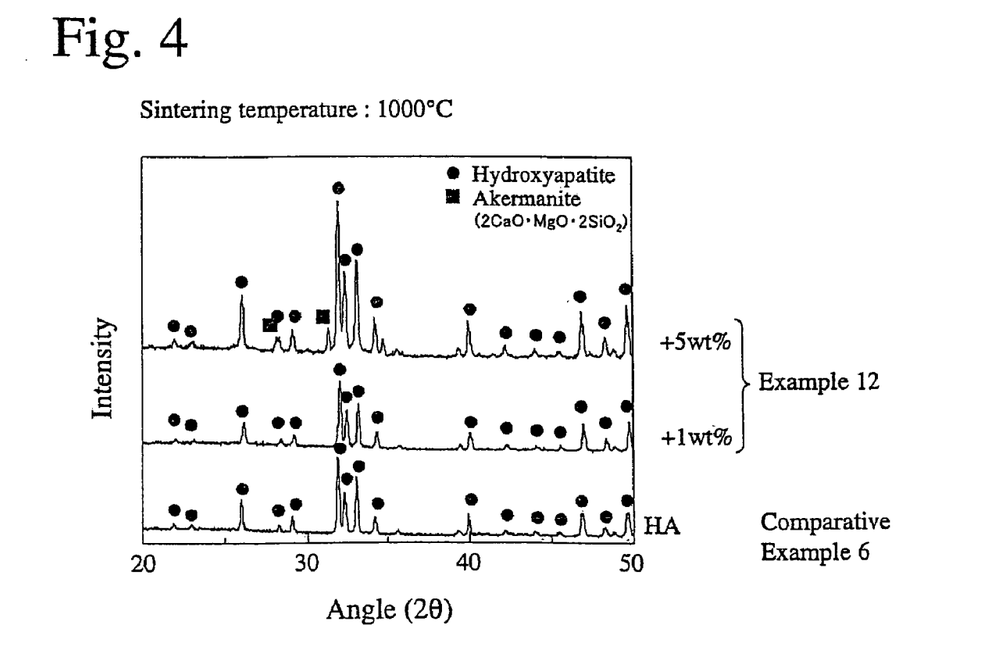
FIG. 4 is a graph showing the results of X-ray structure analysis of those sintered at 1,000° C., which are a sintered hydroxyapatite (HA), a sintered calcium phosphate glass containing 1% by mass of the bioactive glass of Example 4 (indicated by "+1 wt. %"), and a sintered calcium phosphate glass containing 5% by mass of the bioactive glass of Example 4 (indicated by "+5 wt. %")
Figure 5:
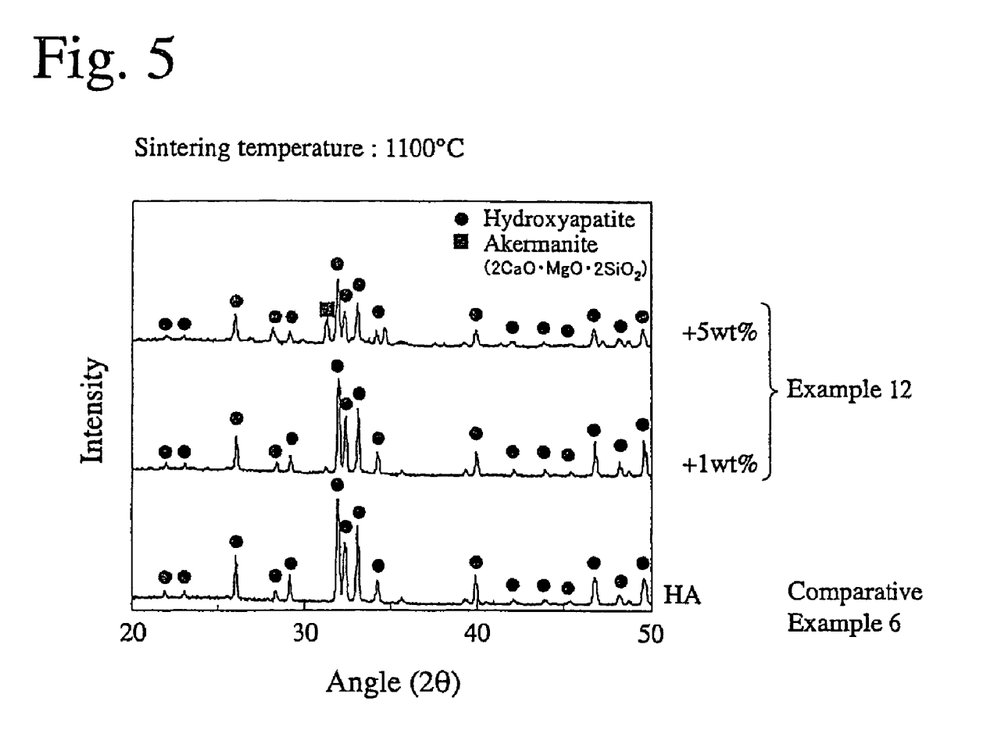
FIG. 5 is a graph showing the results of X-ray structure analysis of those sintered at 1,100° C., which are a sintered hydroxyapatite (HA), a sintered calcium phosphate glass containing 1% by mass of the bioactive glass of Example 4 (indicated by "+1 wt. %"), and a sintered calcium phosphate glass containing 5% by mass of the bioactive glass of Example 4 (indicated by "+5 wt. %").

As shown in FIGS. 3 to 5, the sintered hydroxyapatite bodies of Comparative Example 6 showed only peaks of the hydroxyapatite irrespective of the sintering temperature. Among the sintered hydroxyapatite bodies of Example 12, those produced by mixing 5% by mass of the bioactive glass and sintering at 1,000° C. or 1,100° C., showed peaks of akermanite in addition to the peaks of the hydroxyapatite.

The present disclosure relates to a subject matter contained in Japanese Patent Application No. 2003-354023 (filed on Oct. 14, 2003), which is expressly incorporated herein by reference in its entirety.

What is claimed is:

1. A sintered calcium phosphate comprising a bioactive glass as a sintering aid, said bioactive glass formed from a composition comprising 20 to 40 mol % of CaO, 40 to 60 mol % of $SiO_2$, and 10 to 20 mol % of MgO, further comprising 0.1 to 5 mol % of $Na_2O$, wherein said sintered calcium phosphate is formed from at least one calcium phosphate component selected from hydroxyapatites, carbonated apatites and tricalcium phosphate.

2. The sintered calcium phosphate according to claim 1, wherein said composition forming said bioactive glass further comprises $CaF_2$.

3. The sintered calcium phosphate according to claim 1, wherein said composition forming said bioactive glass further comprises $B_2O_3$.

4. The sintered calcium phosphate according to claim 1, wherein said bioactive glass has a glass transition temperature of 650 to 750° C.

5. The sintered calcium phosphate according to claim 1, wherein a difference between glass transition temperature and crystallization initiation temperature in said bioactive glass is 70 to 250° C.

6. The sintered calcium phosphate according to claim 4, wherein said bioactive glass generates a β-wollastonite crystal and a diopside crystal.

7. The sintered calcium phosphate according to claim 1, wherein said composition forming said bioactive glass contains 5 mol % or less of $P_2O_5$.

8. The sintered calcium phosphate according to claim 1, wherein a β-wollastonite crystal and a diopside crystal are generated in said bioactive glass.

* * * * *